US011565014B2

(12) United States Patent
White et al.

(10) Patent No.: US 11,565,014 B2
(45) Date of Patent: Jan. 31, 2023

(54) RIGID STERILIZATION CONTAINER WITH REPLACEABLE FILTER ASSEMBLIES

(71) Applicant: GLOBUS MEDICAL, INC., Audubon, PA (US)

(72) Inventors: Mitchell White, Edgewater Park, NJ (US); Richard R. Scargill, Lansdale, PA (US); George M. Patton, Trappe, PA (US)

(73) Assignee: Globus Medical Inc., Audubon, PA (US)

( * ) Notice: Subject to any disclaimer, the term of this patent is extended or adjusted under 35 U.S.C. 154(b) by 243 days.

(21) Appl. No.: 16/993,910

(22) Filed: Aug. 14, 2020

(65) Prior Publication Data
US 2020/0405900 A1  Dec. 31, 2020

Related U.S. Application Data

(63) Continuation of application No. 15/399,774, filed on Jan. 6, 2017, now Pat. No. 10,772,982.
(Continued)

(51) Int. Cl.
| E05B 65/00 | (2006.01) |
| A61L 2/26  | (2006.01) |
| A61B 50/30 | (2016.01) |
| B01D 46/00 | (2022.01) |
| A61B 50/00 | (2016.01) |

(52) U.S. Cl.
CPC ............ *A61L 2/26* (2013.01); *A61B 50/30* (2016.02); *B01D 46/0005* (2013.01); *E05B 65/00* (2013.01); *A61B 2050/0067* (2016.02); *A61B 2050/3011* (2016.02); *A61L 2202/24* (2013.01); *Y10T 292/0834* (2015.04); *Y10T 292/0836* (2015.04); *Y10T 292/0846* (2015.04); *Y10T 292/096* (2015.04); *Y10T 292/097* (2015.04); *Y10T 292/0962* (2015.04);
(Continued)

(58) Field of Classification Search
CPC ... A61L 2/26; A61B 50/30; A61B 2050/0067; A61B 2050/3011; A61B 2202/122; A61B 2202/24; B01D 46/0005; E05B 65/00; Y10T 292/0834; Y10T 292/0836; Y10T 292/0845; Y10T 292/0846; Y10T 292/0997; Y10T 292/096; Y10T 292/0962; Y10T 292/0969; Y10T 292/097; Y10T 292/0972; Y10T 292/0975; Y10T 292/0995
See application file for complete search history.

(56) References Cited

U.S. PATENT DOCUMENTS

| 370,331 A | * | 9/1887 | Hamilton | ................ E05B 59/00 27/DIG. 1 |
| 597,574 A | * | 1/1898 | Dick | ..................... A47J 45/071 220/759 |

(Continued)

FOREIGN PATENT DOCUMENTS

DE     102009013442 A1     9/2010

*Primary Examiner* — Christine M Mills
*Assistant Examiner* — Faria F Ahmad

(57) ABSTRACT

Sterilization containers, components, and methods thereof. A locking mechanism is used to secure and release a filter assembly on a sterilization container includes two opposing buttons that, when compressed toward each other, unlock the locking mechanism and, when released, secure the locking mechanism.

20 Claims, 13 Drawing Sheets

Related U.S. Application Data

(60) Provisional application No. 62/350,362, filed on Jun. 15, 2016.

(52) U.S. Cl.
CPC .... *Y10T 292/0969* (2015.04); *Y10T 292/0995* (2015.04); *Y10T 292/0997* (2015.04)

(56) References Cited

U.S. PATENT DOCUMENTS

| | | | | | |
|---|---|---|---|---|---|
| 630,414 | A * | 8/1899 | Schwartz | | A47J 36/08 292/42 |
| 662,681 | A * | 11/1900 | Sigley | | E05B 65/0007 292/42 |
| 907,085 | A * | 12/1908 | McNutt | | E05B 65/0007 292/42 |
| 972,765 | A * | 10/1910 | Hiering et al. | | E05C 1/04 292/42 |
| 1,113,479 | A * | 10/1914 | Phipps | | E05B 67/383 292/148 |
| 1,892,743 | A * | 1/1933 | Wenger | | B65D 45/28 220/323 |
| RE21,608 | E * | 10/1940 | Brinton | | E05B 63/18 292/169.14 |
| 2,221,110 | A * | 11/1940 | Ross | | E05C 1/14 292/164 |
| 2,535,275 | A * | 12/1950 | Thomas | | E02D 29/1427 292/37 |
| 2,878,389 | A * | 3/1959 | Raffman | | G03B 42/04 378/188 |
| 4,312,528 | A * | 1/1982 | Hall | | E05B 65/1053 292/168 |
| 4,341,436 | A * | 7/1982 | Kanno | | G02B 23/16 359/511 |
| 4,600,278 | A * | 7/1986 | Saito | | G02B 23/16 359/511 |
| 4,796,778 | A * | 1/1989 | Habig | | A61L 2/26 220/326 |
| 4,930,819 | A * | 6/1990 | Sharp | | E05C 1/04 292/42 |
| 5,016,926 | A * | 5/1991 | Sharp | | A01K 1/0245 292/42 |
| 5,209,168 | A * | 5/1993 | Chapron | | E05B 17/2084 70/144 |
| 5,681,066 | A * | 10/1997 | Anderson | | E05C 1/166 292/35 |
| 5,736,043 | A * | 4/1998 | Nichols | | A61L 2/06 55/504 |
| 5,868,445 | A * | 2/1999 | Kaufman | | A45C 13/1069 292/42 |
| 6,047,999 | A * | 4/2000 | Dixon, Jr. | | E05B 63/18 292/42 |
| 6,056,684 | A * | 5/2000 | Linder | | B04B 7/02 494/12 |
| 6,622,871 | B2 * | 9/2003 | Gabele | | A61L 2/26 422/534 |
| 6,880,718 | B2 * | 4/2005 | Eggum | | H01L 21/67373 220/323 |
| 6,994,128 | B2 * | 2/2006 | Gleichauf | | A61L 2/26 141/66 |
| 7,036,678 | B2 * | 5/2006 | Eiskant | | A61B 50/31 220/795 |
| 7,077,270 | B2 * | 7/2006 | Matsutori | | H01L 21/67376 206/711 |
| 7,182,203 | B2 * | 2/2007 | Burns | | E05B 17/0041 220/326 |
| 7,381,385 | B2 * | 6/2008 | Gleichauf | | A61L 2/26 422/297 |
| 7,585,005 | B1 * | 9/2009 | Cote | | E05C 1/10 312/265.5 |
| 7,971,723 | B1 * | 7/2011 | Chiu | | H01L 21/67373 206/711 |
| 8,276,758 | B2 * | 10/2012 | Lin | | H01L 21/67373 220/323 |
| 2001/0020601 | A1 * | 9/2001 | Gabele | | A61L 2/26 210/348 |
| 2005/0183479 | A1 * | 8/2005 | Alacqua | | E05B 47/0009 70/277 |
| 2012/0193364 | A1 * | 8/2012 | Zhong | | A47J 27/002 220/573.1 |

* cited by examiner

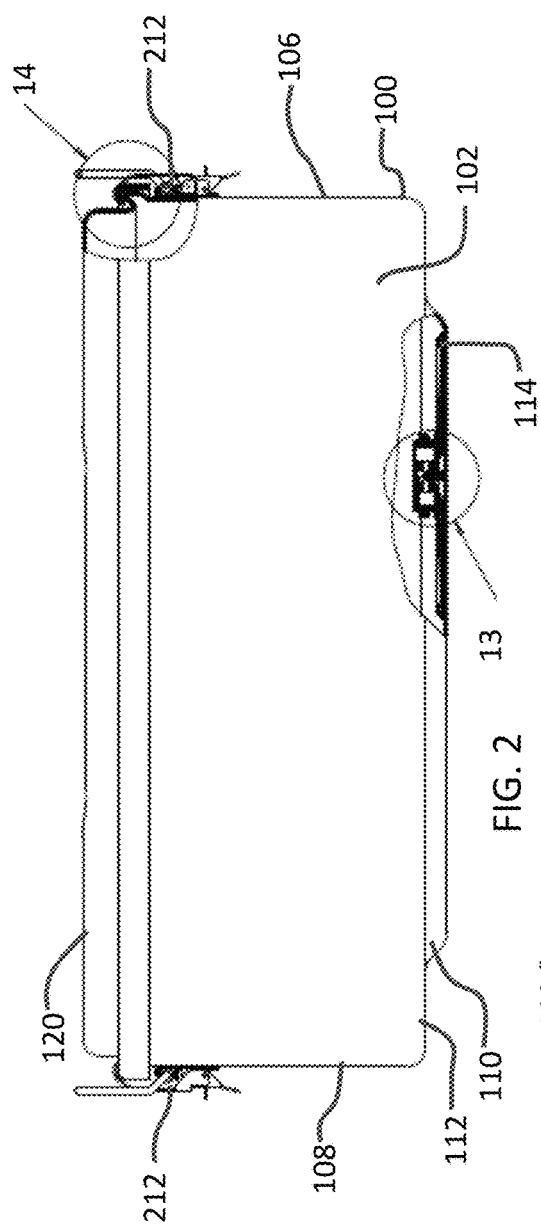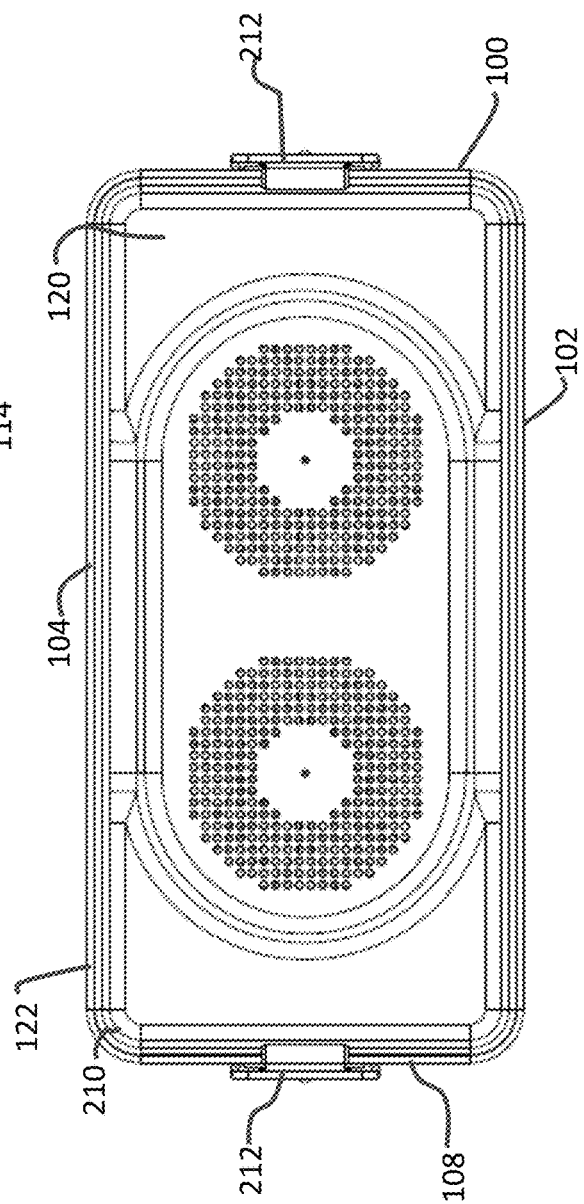

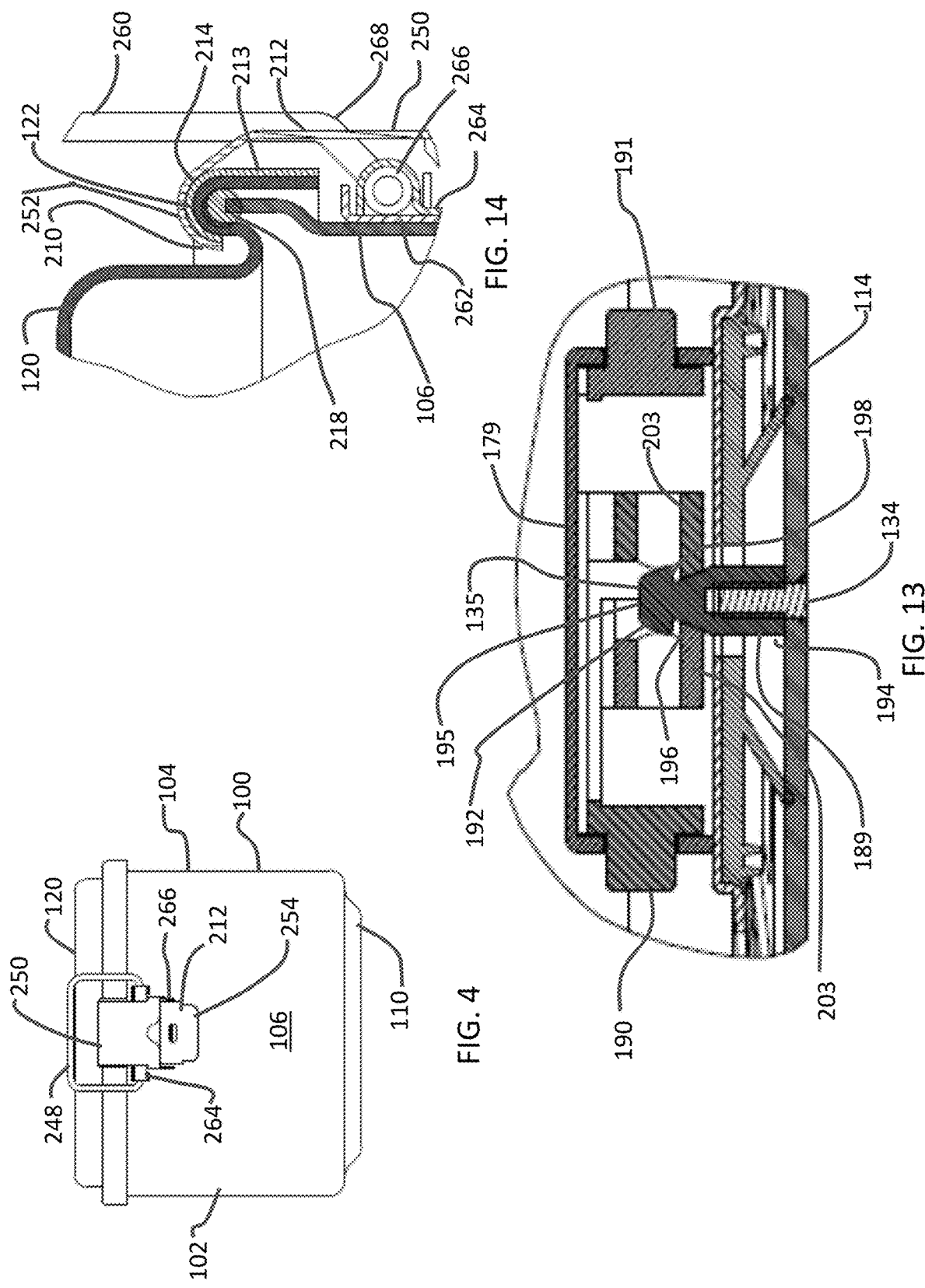

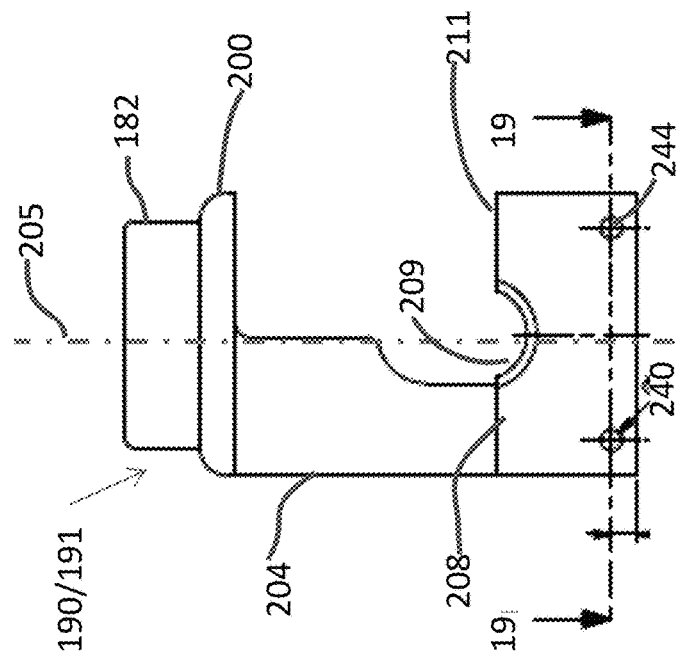
FIG. 17
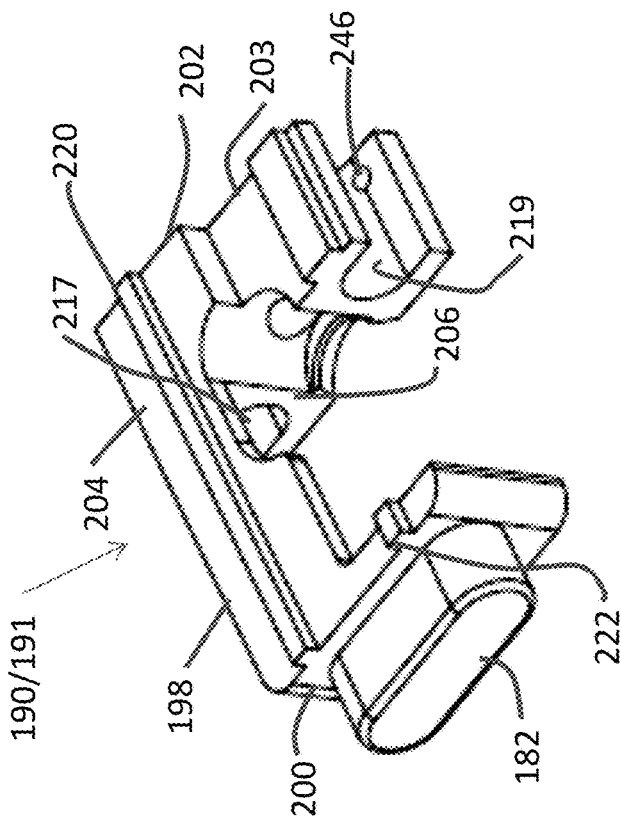
FIG. 16
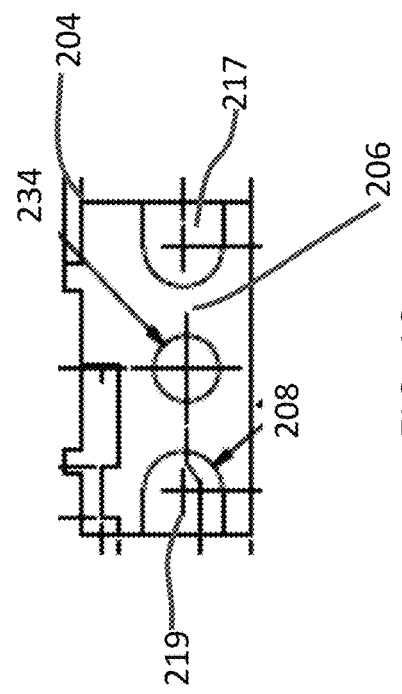
FIG. 18
FIG. 19

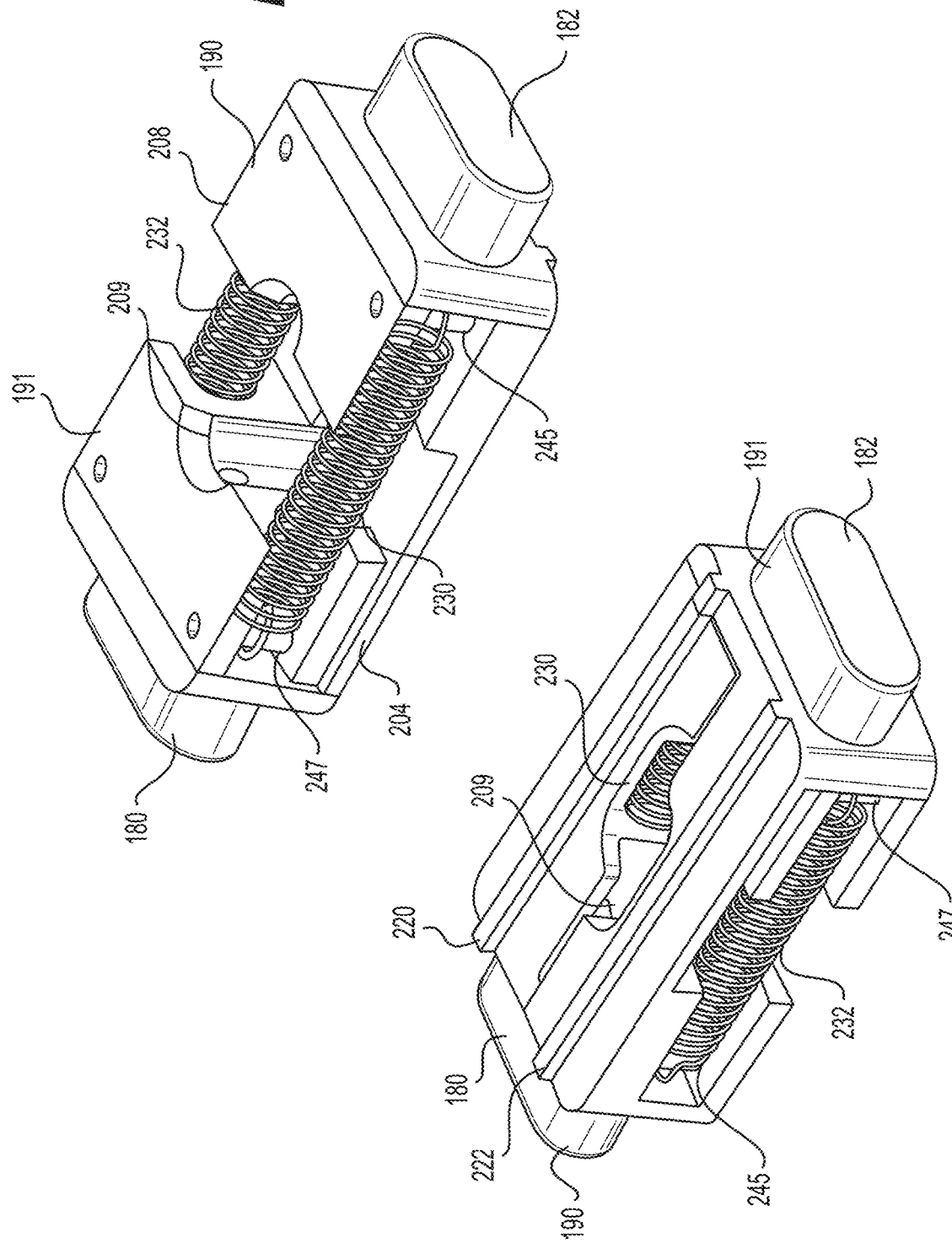

RIGID STERILIZATION CONTAINER WITH REPLACEABLE FILTER ASSEMBLIES

CROSS-REFERENCE TO RELATED APPLICATION

This application is a continuation of U.S. Ser. No. 15/399,774 filed on Jan. 6, 2017 (published as U.S. Pat. Pub. No. 2017-0360975), which is a non-provisional application that claims priority to provisional application No. 62/350,362, filed Jun. 15, 2016, all of which are hereby incorporated by reference in their entireties for all purposes.

BACKGROUND

Field of the Invention

The present invention relates to containers, and more specifically, to sterilization containers that can be used to sterilize and store medical devices, for example.

Description of the Related Art

Sterilization containers include air permeable filter assemblies that allow filtered ambient air to enter and exit the container during and after the sterilization process. After a use, it may be desirable to re-use the container. However, it would be desirable to be able to replace the filter media in the filter assemblies to ensure a clean transfer of sufficient air through the filter assemblies.

Accordingly, there exists a need for a sterilization container that includes filter assemblies that can be readily removed and replaced if necessary.

SUMMARY

To meet this and other needs, devices, systems, and methods of sterilization are provided. The sterilization devices and systems may include a sterilization container, one or more filters, one or more filter retaining plates, and one or more clips or locks designed to secure the filters and/or plates to the sterilization container. The methods may include steps for assembling and/or utilizing the sterilization container, for example, in an autoclave process.

According to one embodiment, a sterilization container may include a pan, lid, filter retaining plates, filter retainer clips, seals, and handles. The pan contains holes that permit the passage of air, moist heat/steam, or other autoclave gases into the container. The retaining plates attach to the pan over these perforated areas to hold filter media.

In one embodiment, the sterilization container includes a locking mechanism comprising a shell and a first clip slidingly inserted inside the shell. The first clip has a first locking member. A second clip is slidingly inserted inside the shell. The second clip has a second locking member. A biasing member has a first end connected to the first clip and a second end connected to the second clip such that the biasing member biases the first clip and the second clip such that the first locking member is biased toward the second locking member.

In another embodiment, the sterilization container includes a locking mechanism comprising a shell having a first opening, a second opening, and a cavity extending between the first opening and the second opening. A first clip has a first button extending through the first opening, a first elongate base extending distally from the first button, a first spacer extending from the first base, a first surface extending upwardly from the first spacer. The first surface has a first cavity formed at a first proximal end thereof. A first biasing member support is disposed between the first elongate base and the first surface. A second clip is identical to the first clip. A biasing member has a first end connected to the first biasing member support and a second end connected to a second biasing member support.

In still another embodiment, the sterilization container includes a locking assembly comprising a mounting post and a locking mechanism. The locking mechanism comprises a shell and a first clip slidingly inserted inside the shell. The first clip has a first locking member disposed on a first side of the mounting post. A second clip is slidingly inserted inside the shell. The second clip is identical to the first clip and is disposed on an opposing side of the mounting post. A biasing member has a first end connected to the first clip and a second end connected to the second clip such that the biasing member biases the first clip and the second clip into engagement with the mounting post.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 2 is a front elevational view of the sterilization container shown in FIG. 1;

FIG. 3 is a top plan view of the sterilization container shown in FIG. 1;

FIG. 4 is a right side elevational view of the sterilization container shown in FIG. 1;

FIG. 13 is an enlarged sectional view of the filter assembly of FIG. 8, taken along enlargement circle 13 shown in FIG. 2;

FIG. 14 is an enlarged sectional view of a lid clip used with the container taken along enlargement circle 14 of FIG. 2;

FIG. 16 is an exploded perspective view of a clip used with the locking mechanism shown in FIG. 15;

FIG. 17 is a bottom plan view of the clip shown in FIG. 16;

FIG. 18 is an end elevation view of the clip shown in FIG. 16;

FIG. 19 is a sectional view of the clip shown in FIG. 16, taken along lines 19-19 of FIG. 17;

FIG. 24 is a is a bottom perspective view of the locking mechanism shown in FIG. 15, without it shell, showing the clips in an unlatching position; and FIG. 25 is a top perspective view of the locking mechanism of FIG. 24.

DETAILED DESCRIPTION

Figure 1:
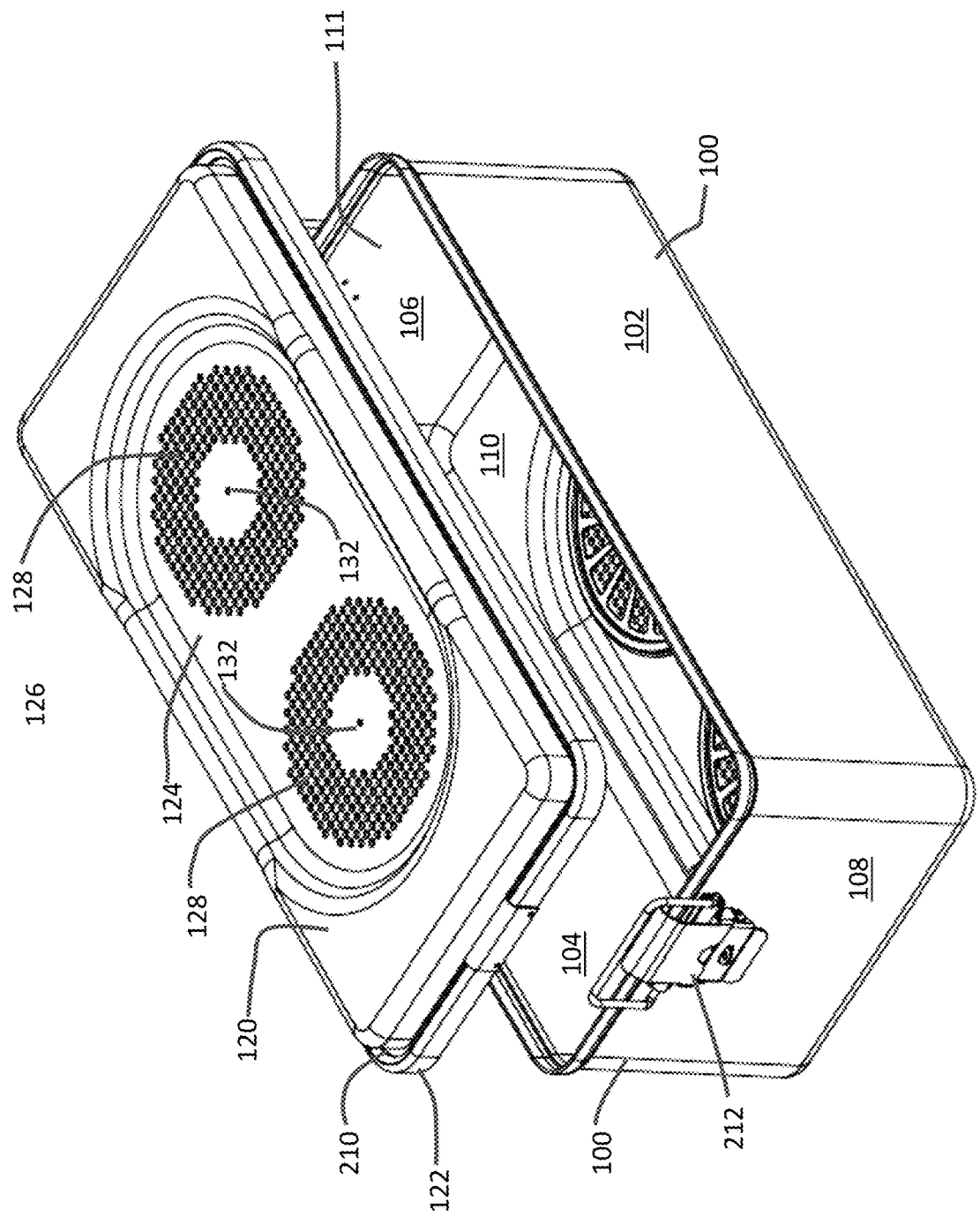
FIG. 1 is a perspective view of a sterilization container according to a first exemplary embodiment.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed of joining or connecting two or more elements directly or indirectly to one another, and the interposition of one or more additional elements is contemplated, although not required. Conversely, the terms "directly coupled," "directly connected," etc., imply the absence of such additional elements.

The present disclosure provides embodiments of autoclavable containers that can be used to sterilize and store medical devices and/or medical instruments, for example. The containers may be especially configured to hold product graphic cases during a steam sterilization cycle, for example, as an alternative to using sterilization wraps.

Exemplary specifications for inventive containers may include, for example: permitting penetration of a sterilizing medium, e.g., steam sterilization, and allow for drying of moisture left behind by the sterilization within standard autoclave times; having a minimum filter area configured for effective sterilization of the devices and instruments positioned within a graphic case within the sterilization device, e.g., a minimum filter area of 176 square inches; allowing one or more product graphic cases to fit with their handles in an upright position; utilizing standard filter sizes and tamper proof locks; weighing not more than 11 pounds for the largest size; and being stackable.

Such containers also include filter assemblies that allow for the passage of a sterilization medium, such as steam and air, into and out of the containers during and after a sterilization process. When the container is sealed with its lid, the filter assemblies may be the only locations on the container that allow the passage of moist heat. This ensures that the contents within the container remain sterile once removed from the autoclave.

According to one embodiment, a filter assembly may include a filter assembly clip that securely retains the filter assembly on the container, yet can be readily released to remove the filter assembly from the container for replacement of its filter media.

Referring to FIGS. 1-4, a container 100 according to a first exemplary embodiment is shown. Container 100 provides an alternate to traditional sterilization wraps for hospitals. Some benefits of container 100 over the prior art container include a lightweight design that weighs less than some other known containers; a lid design that allows the handles of a case (not shown) that is placed inside container 100 to remain upright, allow the surgical staff to easily lift the case out of container 100 in an operating room environment; the bottom of the pan mirrors the shape of the lid, allowing a second container 100 to be easily stacked on a first container 100 for storage; accommodation of standard filters and tamper locks, thereby allowing hospitals to easily integrate container 100 into the sterile processing departments; and a proven latch design for longevity.

Container 100 is a generally parallelepiped structure having longitudinal front and rear sides 102, 104, respectively, lateral right and left sides 106, 108, respectively, and a bottom pan 110. Sides 102, 104, 106, 108 and bottom pan 110 define a cavity 111 into which objects, such as product graphic cases (not shown) to be stored within container 100.

Figure 5:
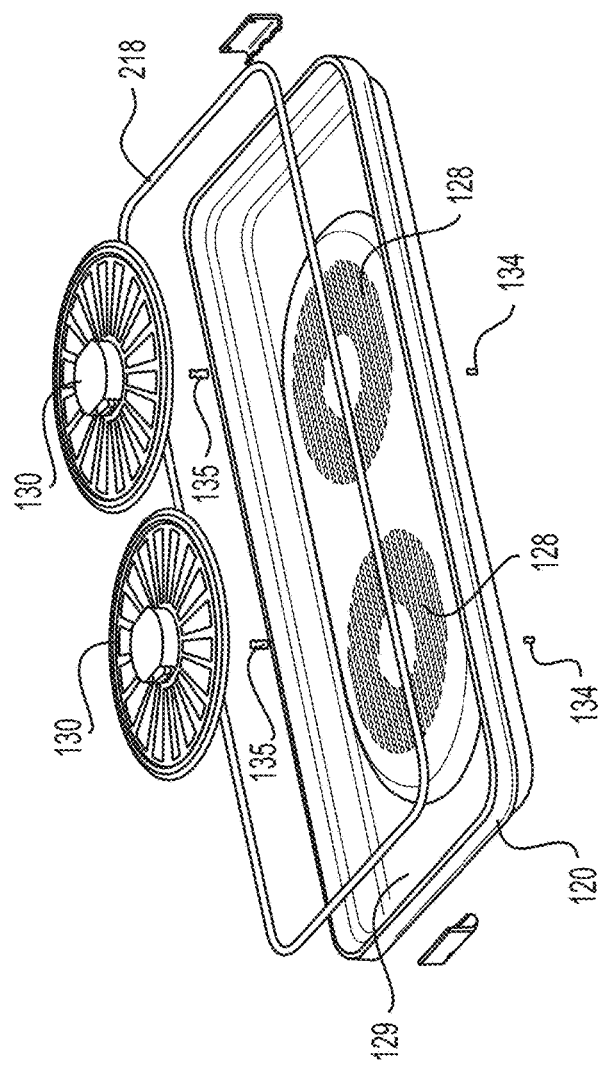
FIG. 5 is a bottom perspective exploded view of a lid used with the container shown in FIG. 1.
Figure 6:
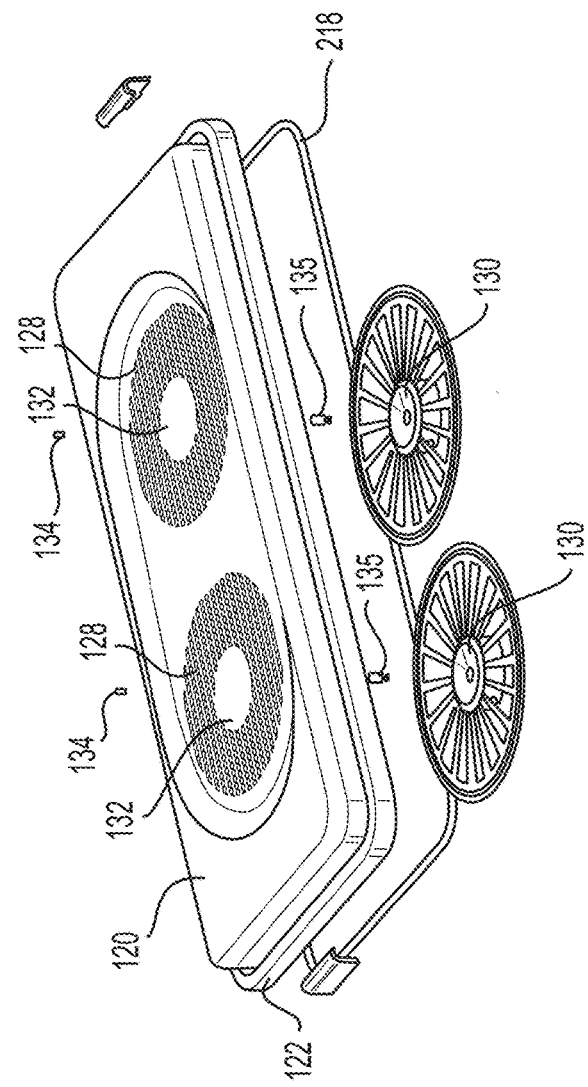
FIG. 6 is a top perspective exploded view of the lid shown in FIG. 5.

Referring to FIGS. 5 and 6, a removable lid 120 is provided to cover container 100. Bottom pan 110 includes a rim 112 that extends around a perimeter thereof, defining a projection 114 extending downwardly from bottom pan 110. Similarly, lid 120 includes a rim 122 defining an indentation 124 extending downwardly from a top surface 126 of lid 120 such that projection 114 of one container 100 can fit into indentation 124 of another container 100, allowing a plurality of containers 100 to be stacked, one on top of another.

Each indentation 124 includes two sets of a plurality of openings 128 arranged in a generally annular pattern. Openings 128 allow air passage through lid 120 and to/from filter assemblies 130 mounted on an interior 129 of lid 120. A screw hole 132 is centered within each plurality of openings 128 to allow for the passage of a securing member, such as a screw 134, to secure a mounting post 135 to lid 120. Filter assemblies 130 are sized so as not to project significantly above projection 114 so as not to take up a significant amount of space within cavity 111.

Figure 7:
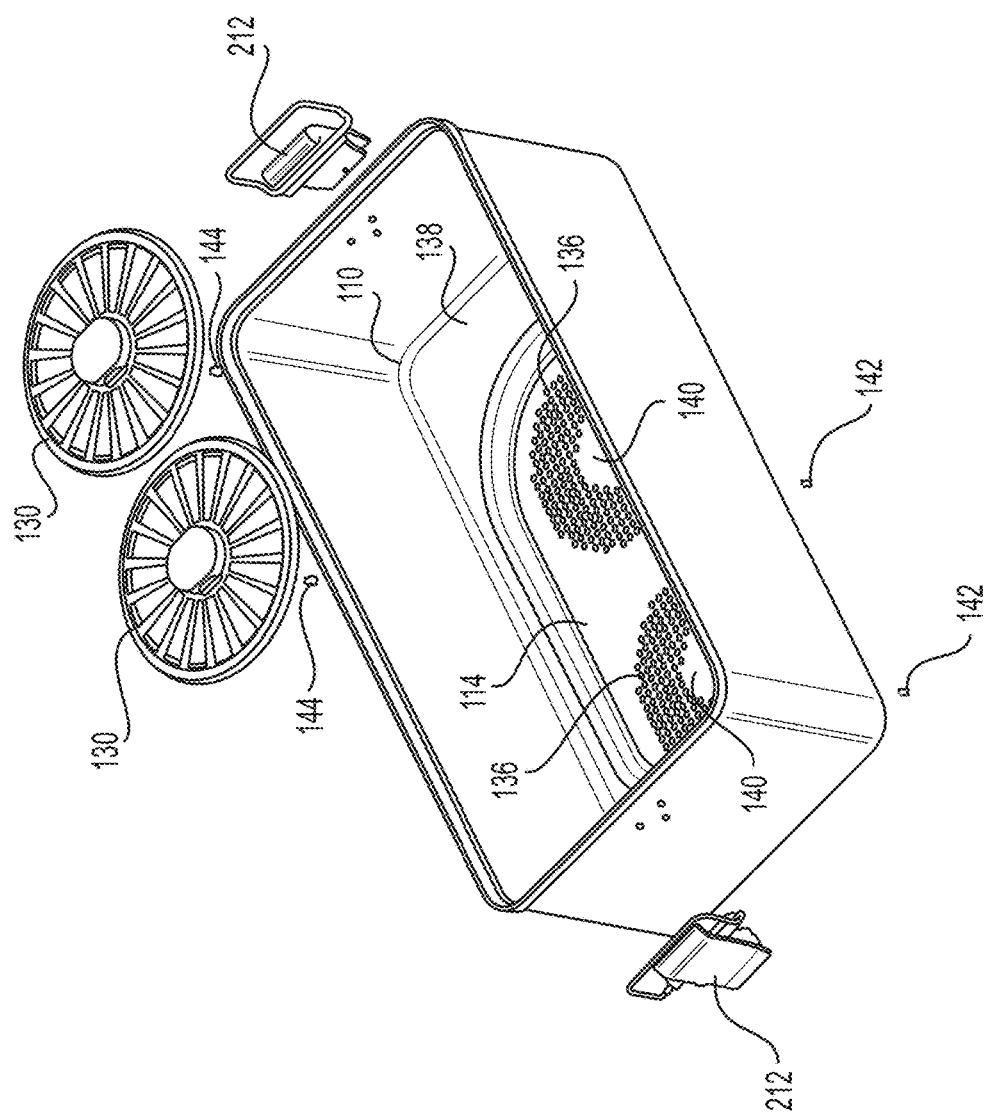
FIG. 7 is a top perspective exploded view of the container shown in FIG. 1.
Figure 8:
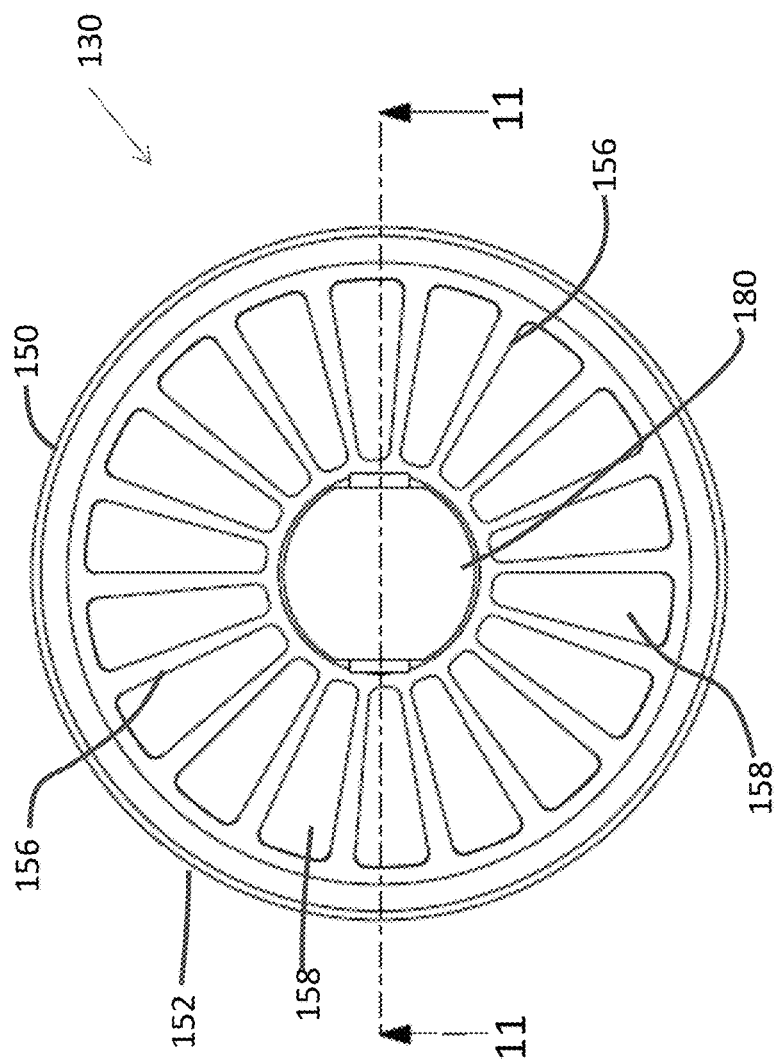
FIG. 8 is a top plan view of a filter assembly used with the container shown in FIG. 1.
Figure 9:
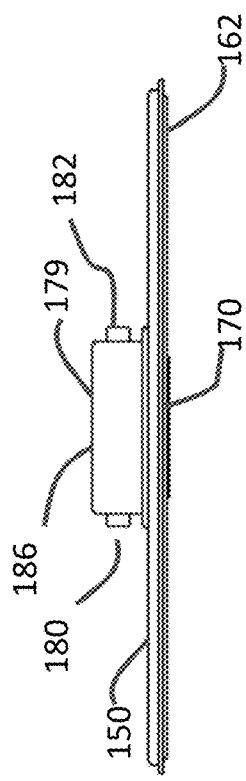
FIG. 9 is a side elevational view of the filter assembly shown in FIG. 8.
Figure 10:
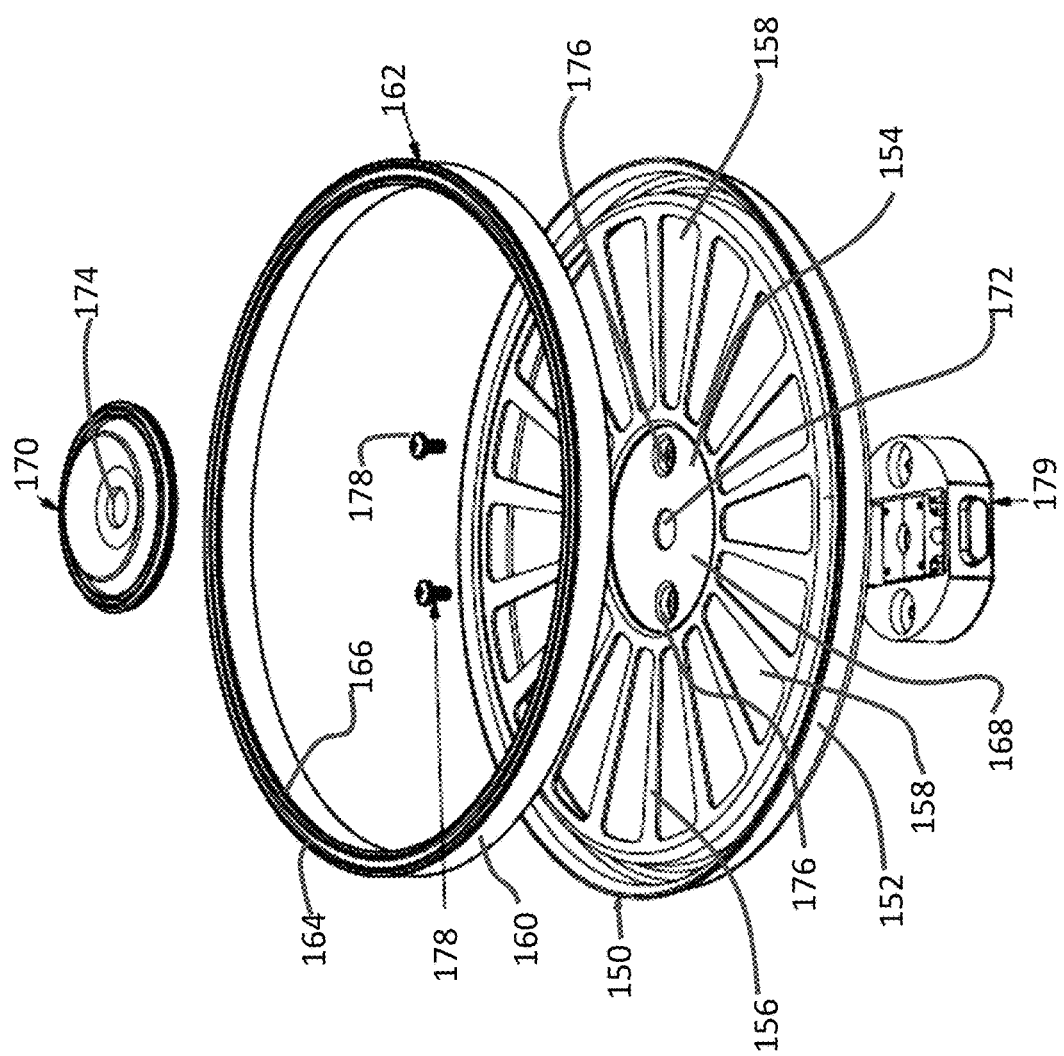
FIG. 10 is a top exploded view of the filter assembly shown in FIG. 8.
Figure 11:
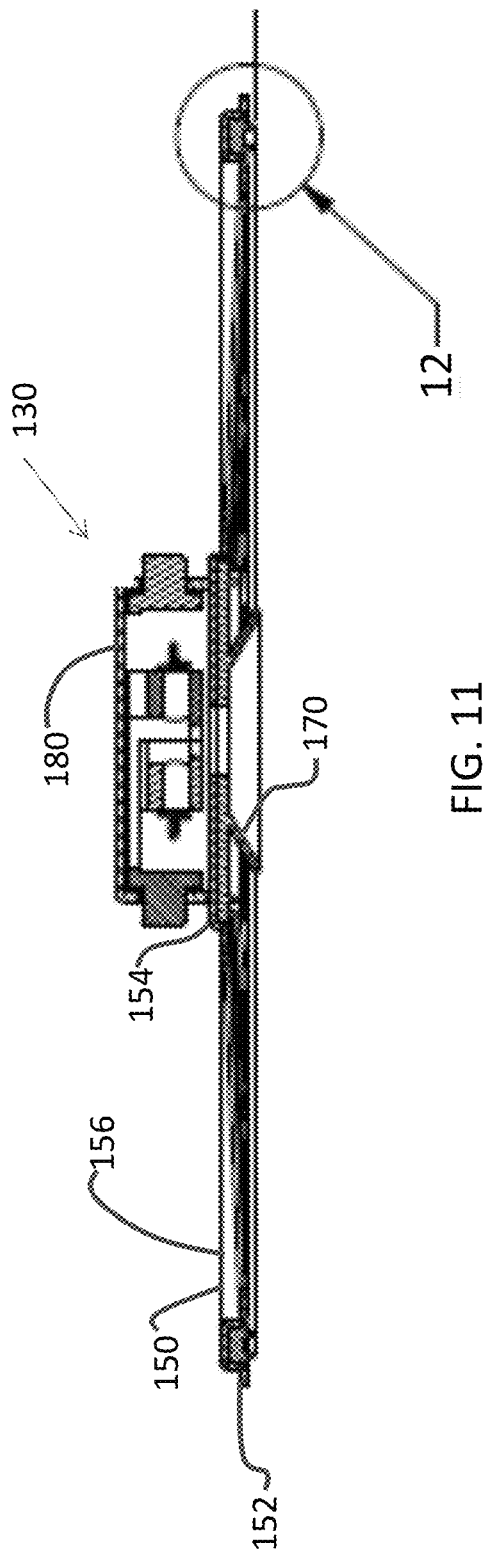
FIG. 11 is a sectional view of the filter assembly taken along lines 11-11 of FIG. 8.
Figure 12:
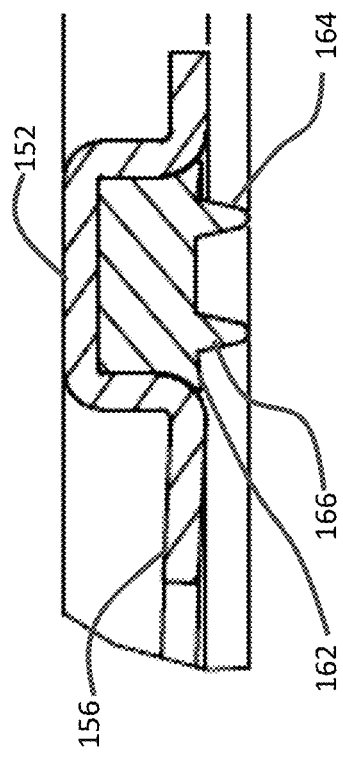
FIG. 12 is an enlarged view of a seal used with the filter assembly of FIG. 8, taken along enlargement circle 12 shown in FIG. 11.

Similarly, referring to FIG. 7, projection 114 includes two sets of a plurality of openings 136 arranged in a generally annular pattern. Openings 136 allow air passage through bottom pan 110 and to/from filter assemblies 130 mounted on an interior 138 of bottom pan 110. A screw hole 140 is centered within each plurality of openings 136 to allow for the passage of a securing member, such as a screw 142, to secure a mounting post 144 to bottom pan 110.

Referring to FIGS. 8-13, filter assembly 130 includes a generally circular retainer disk 150 having an outer perimeter 152, a central hub 154, and a plurality of spokes 156 connecting central hub 154 to outer perimeter 152. A filter media 158 is disposed between adjacent spokes 156. Retainer disk 150 can be sized to hold standard 7.5 inch diameter filter media offered by various manufacturers.

Outer perimeter 152 includes a recessed channel 160 sized to receive and retain an outer seal 162. Outer seal 162 is annular in shape and includes an outer lip 164 and an inner lip 166. Outer seal 162 can be constructed from silicone, rubber, or other suitable sealing material.

Hub 154 includes a recessed surface 168 that is sized to accept an inner seal 170. Hub 154 includes a central opening 172 that is sized to allow mounting post 135, 144 to extend therethrough. Similarly, inner seal 170 includes a central opening 174 that is also sized to allow mounting post 135, 144 to extend therethrough. Inner seal 170 can be constructed form silicone, rubber, or other suitable material.

Referring specifically to FIG. 13, mounting post 135 is shown. In an exemplary embodiment, mounting post 144 is identical to mounting post 135, so only mounting post 135 will be discussed. Mounting post 135 includes a connected end 189 and a free end 192. Connected end 189 includes a threaded blind passage 194 into which screw 134 is inserted. Free end 192 includes a frusto-conical head 195 mounted on a tapered support 196. Tapered support 196 extends underneath frusto-conical head 195 such that a rim 198 is formed on the underside of head 195.

Hub 154 also includes a pair of through-openings 176 that are sized to receive securing members, such as screws 178. Screws 178 are used to secure a locking mechanism 179 to hub 154.

Referring to FIGS. 15-25, locking mechanism 179 includes two opposing buttons 182, 184 that, when compressed toward each other, release locking mechanism 179 and, when released, secure locking mechanism 179. As shown in FIG. 16, button 180 is generally parallelepiped in shape, with curved lateral sides, forming an oblong cross-section. Those skilled in the art, however, will recognize that button 182 can be other shapes as well.

Figure 15:
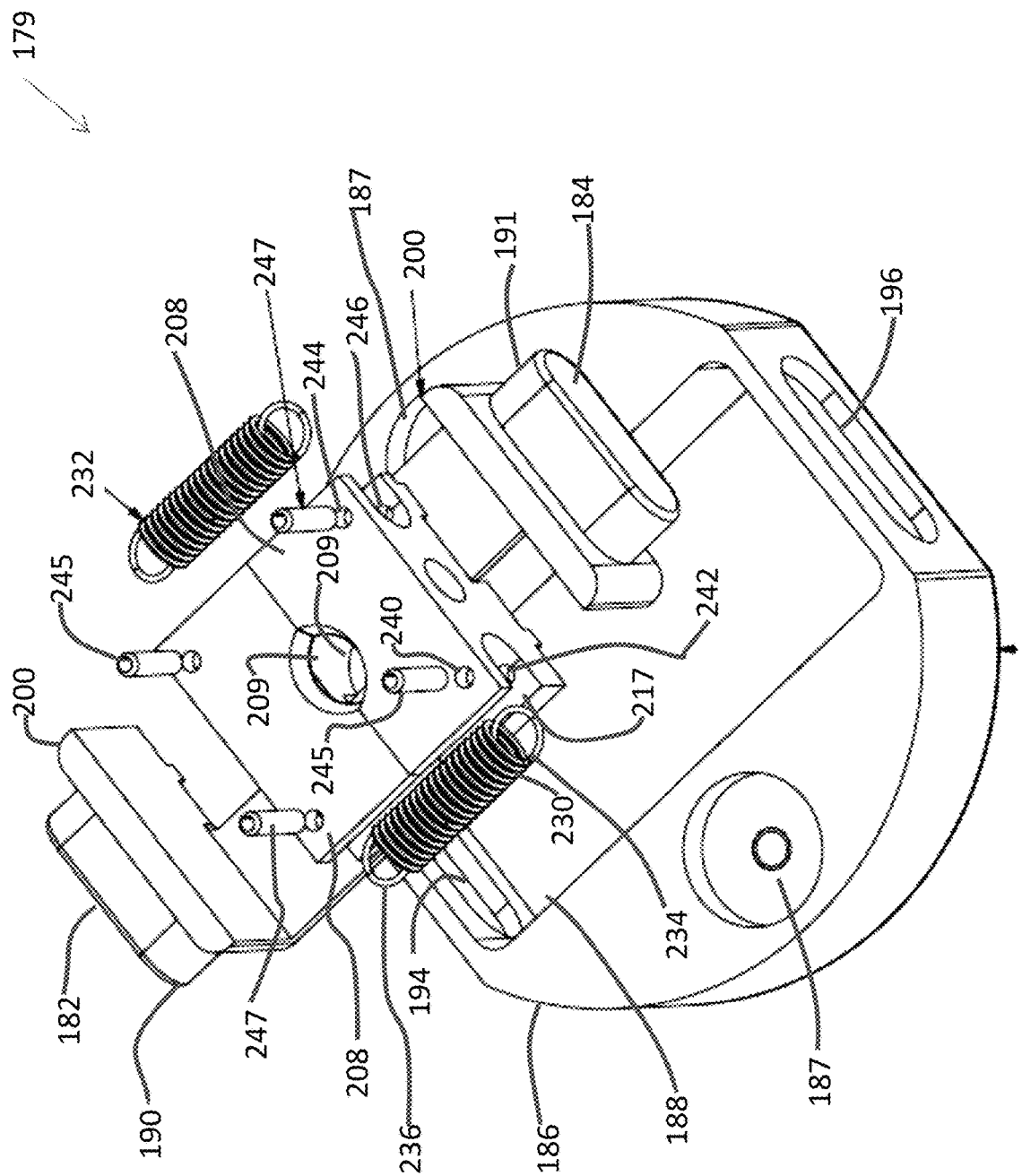
FIG. 15 is an exploded view of an exemplary embodiment of a locking mechanism used to secure the filter assembly of FIG. 8 onto the container of FIG. 1.
Figure 21:
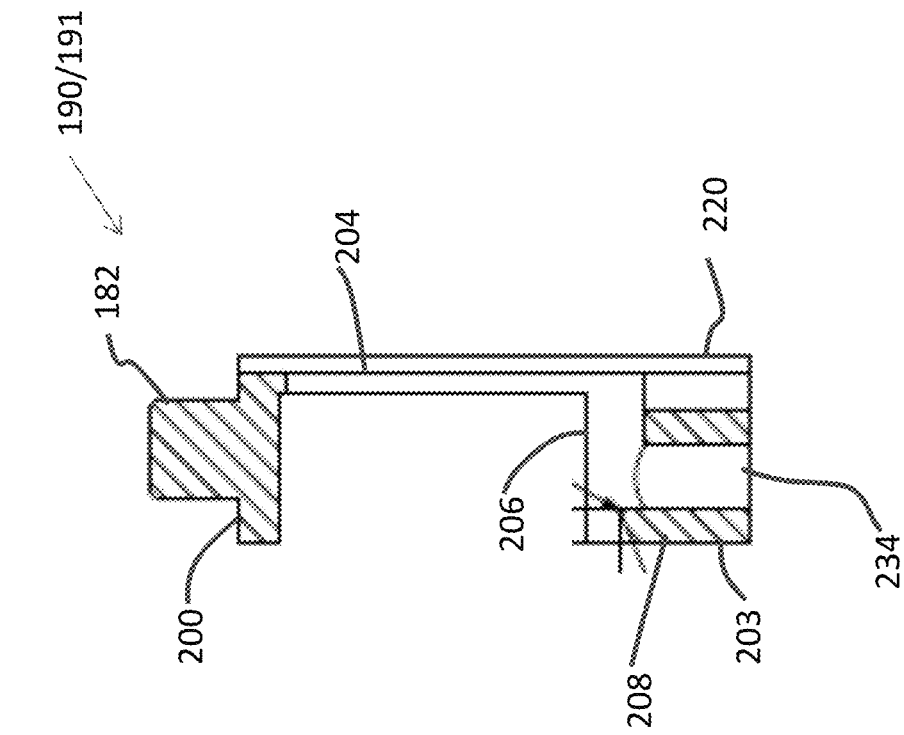
FIG. 21 is a sectional view of the clip shown in FIG. 16, taken along lines 21-21 of FIG. 20.
Figure 20:
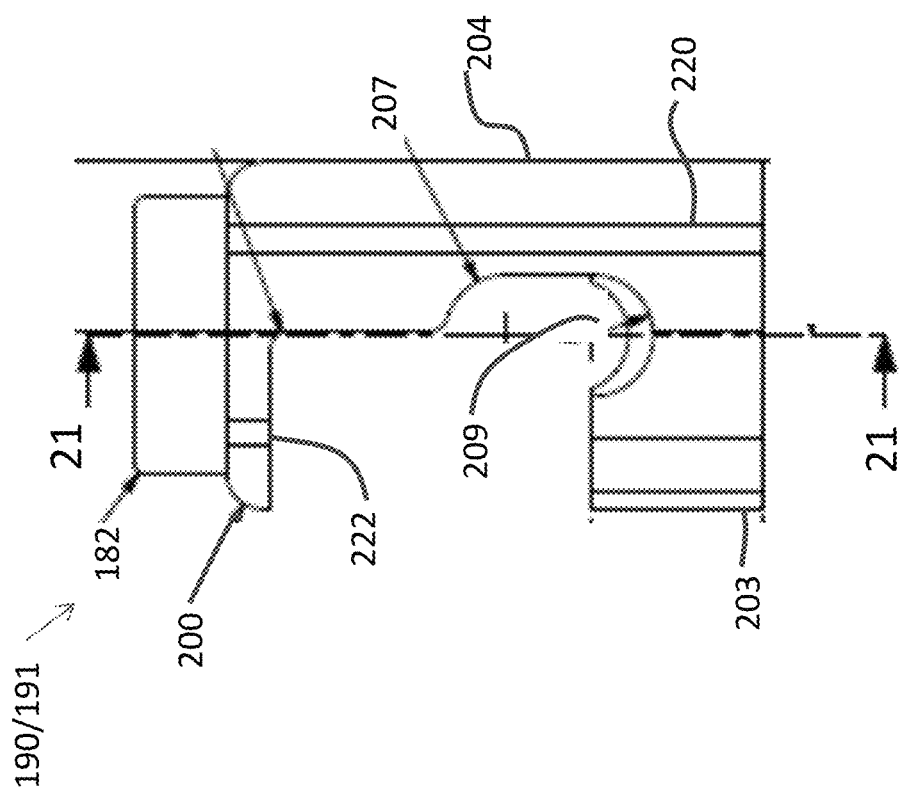
FIG. 20 is a top plan view of the clip shown in FIG. 16.

Buttons 182, 184 are contained in a shell 186 having an elongate cavity 188. As shown in FIG. 15, shell 186 includes a pair of diametrically opposed recesses 187 on either side of cavity 188 that allow for screws 178 (shown in FIG. 10) to secure shell 186 to hub 154. A first clip 190 and a second clip 191 are slidingly disposed inside cavity 188 for longitudinal motion in cavity 188. In an exemplary embodiment, first clip 190 is identical to second clip 191. First clip 190 and second clip 191 are disposed in shell 186 such that first clip 190 and second clip 191 travel in opposing directions, as will be discussed in more detail later herein.

On a first side of cavity 188, shell 186 comprises a first activation opening 194 through which button 182 on first clip 190 slidably extends. Similarly, on a second side of cavity 188, shell 186 comprises a second activation opening 196, diametrically opposite from first activation opening 194, such that cavity 188 extends between first activation opening 194 and second activation opening 196, through which button 184 on second clip 191 slidably extends.

First clip 190 is shown in FIGS. 16-21. Because, in an exemplary embodiment, first clip 190 and second clip 191 are identical, only first clip 190 will be described.

Clip 190 has a body 199 having a proximal end 200 connected to button 182 and a distal end 202 that includes locking member 203. As used herein, the term "proximal" is a location on clip 190, 191 closer to button 180, 182, respectively, and "distal" is a location on clip 190, 191 farther from button 180, 182, respectively.

Body 199 includes an elongate base 204 connected to and extending distally from button 182. Base 204 extends along only one side of a longitudinal axis 205 and includes an elongate void 207 (shown in FIG. 20). An opposing side of longitudinal axis 205 is devoid of a body to provide room for second clip 191. A spacer 206 extends from base 204 and, referring to FIGS. 22 and 24, a surface 208 extends from spacer 206. Surface 208 is a planar surface having a cavity 209 formed at a proximal end 211 thereof such that surface 208 and cavity 209 form locking member 203. Cavity 209 is arcuate in shape and is beveled for engagement with tapered support 196 on mounting post 135. Cavity 209 extends partially around mounting post 135 when clip 190 is engaged with mounting post 135.

A first arcuate passage 217 extends between base 204, spacer 206, and surface 208. First arcuate passage 217 is sized to allow a biasing member, such as a first spring 230, to fit thereinto. Similarly, an opposing side of spacer 206 includes a second arcuate passage 219 that is sized to allow a second spring 232 to fit thereinto. Optionally, a through passage 234 can be formed in spacer 206 between arcuate passages 217, 219. Through passage 234 reduces the amount of material used in body 199 and reduces the weight of body 199, allowing for a smoother operation of clip 190.

Referring to FIG. 16, base 204 includes a plurality of ribs 220, 222 that rest in the bottom of shell 186 and allow clip 190 to slide within shell 186 with less friction than if ribs 220, 222 were omitted and base 204 directly engaged and slid within shell 186.

As shown in FIG. 19, a first pin passage 240 extends through surface 208, coaxially with a first pin slot 242. First pin passage 240 and first pin slot 242 are sized to receive and retain a first biasing member support 245 so that first biasing member support 245 is disposed in first arcuate passage 217 at distal end 202 between elongate base 204 and surface 208. Similarly, a second pin passage 244 extends through surface 208, coaxially with a second pin slot 246. Second pin passage 244 and second pin slot 246 are sized to receive and retain a second biasing member support 247 so that second biasing member support 247 is disposed in second arcuate passage 219 at first distal end 202 between elongate base 204 and surface 208.

As discussed above, in an exemplary embodiment, clip 190 and clip 191 are identical. When clips 190, 191 are assembled in shell 186, surface 208 of first clip 190 is coplanar with a corresponding surface 208 of second clip 191. Cavity 209 on clip 190 and a corresponding cavity 209 on clip 191 form a locking surface that is used to engage mounting post 135. See FIG. 15.

Figure 22:
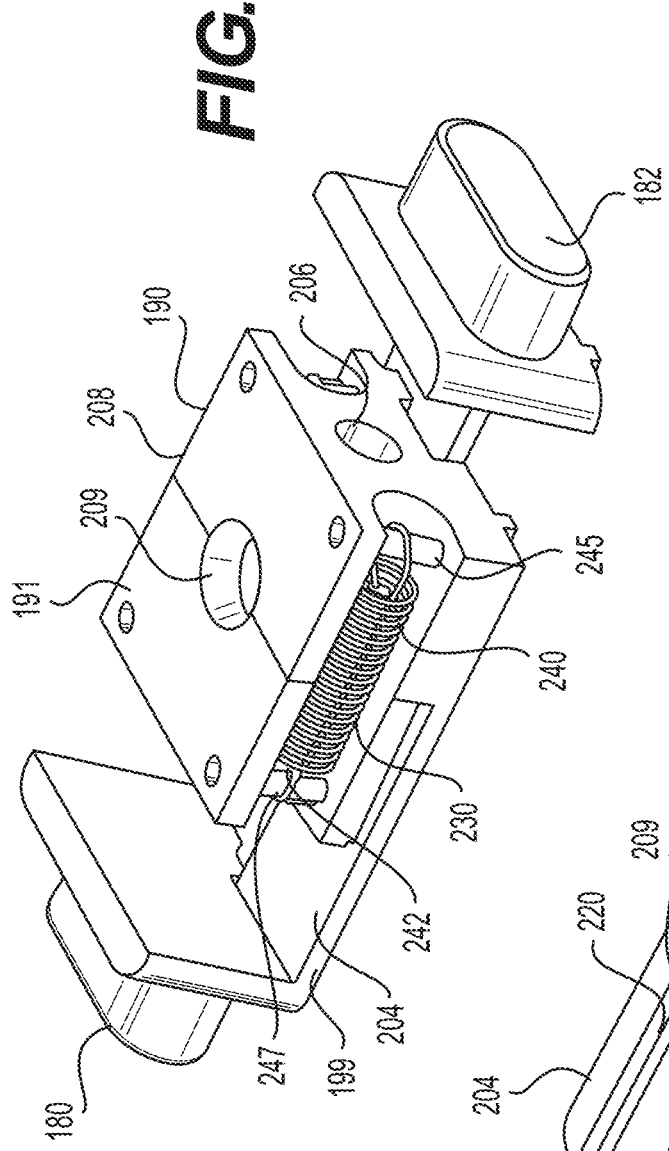
FIG. 22 is a bottom perspective view of the locking mechanism shown in FIG. 15, without its shell, showing the clips in a latching position.
Figure 23:
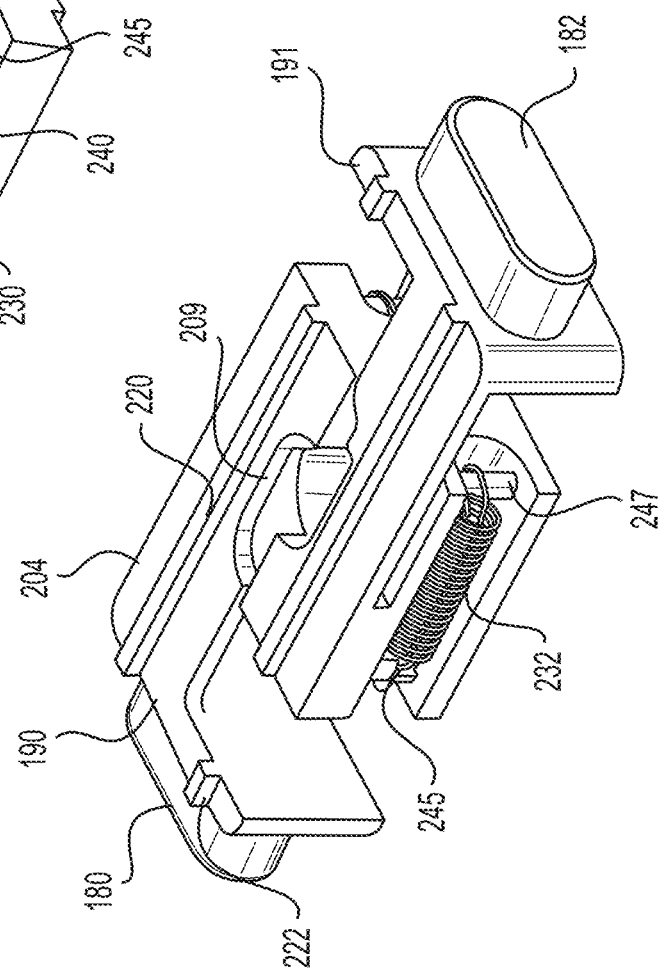
FIG. 23 is a top perspective view of the locking mechanism of FIG. 22.

First biasing member 230 has a first end 234 connected to clip 190 at first biasing member support 245 and a second end 236 connected to clip 191 at second biasing member support 247 such that biasing member 230 biases clip 190 and clip 191 so that surface 208 on clip 190 is biased toward surface 208 on clip 191. In an exemplary embodiment, first biasing member 230, as well as second biasing member 232, is a helical spring disposed in first arcuate passage 217 and second arcuate passage 219, respectively, between base 204 and first locking member 203. Biasing members 230, 232 bias locking member 203 on clip 190 and locking member 203 on clip 191 into engagement with mounting post 135. Referring to FIG. 22, a first portion 240 of biasing member 230 extends through clip 190 and a remaining portion 242 of biasing member 230 extends through clip 191.

When locking mechanism 179 is attached to hub 154, mounting post 135 is disposed between cavity 209 of clip 190 and cavity 209 of clip 191 wherein, when locking mechanism 179 is in a locked position, as shown in FIG. 13, surface 208 of first clip 190 and the first surface 208 of second clip 191 engage mounting post 135. Locking mechanism 179 is shown in a locked position in FIGS. 22 and 23.

Translation of first button 182 and second button 184 into shell 186 moves surface 208 of clip 190 away from mounting post 135 and toward second button 182, as well as moves surface 208 of clip 191 away from mounting post 135 and toward first button 182, releasing locking mechanism 179 from mounting post 135 and allowing locking mechanism 179 to be removed from container 100 or lid 120. FIGS. 24 and 25 show locking mechanism 179 in an unlocked position. This translation extends biasing members 230, 232 between their respective mounting posts 245, 247, storing energy within biasing member 230, 232. When first and second buttons 182, 184 are released, the energy stored in biasing members 230, 232 is released, compressing biasing members 230, 232, and moving locking members 203 of each clip 190, 191 into engagement with mounting post 135.

Referring back to FIG. 14, rim 122 of lid 120 includes a recessed channel 210 extending therearound. Channel 210 is sized to accept a lid lock 212 on right side 106 and a similar lid lock 212 on left side 108 of container 100. A reinforcing member 213 is located over rim 122 and has a first end extending into channel 210 and a second end extending outwardly of lid 120 to the end of rim 122. Reinforcing member 213 can be constructed from aluminum, stainless steel, or other suitable material.

Rim 122 also includes a convex portion 214 that is sized to accept and retain a seal 218. Seal 218 seals the space between container 100 and lid 120 when lid is secured to container 100. Seal 218 can be constructed from silicone, rubber, or other suitable material.

Referring back to FIGS. 2, 4, and 14, lid lock 212 includes a latching portion 250 having a free end 252 that engages reinforcing member 213, as shown in FIG. 14. An opposing end of latching portion 250 is cammed to a lever 264 at a pivot 266 such that, as lever 264 is pushed downward to the position shown in FIG. 2, free end 252 biases downwardly against reinforcing member 213, securing lid 120 to container 100. To release latching portion 250, lever 264 is pushed upward, releasing the camming action at pivot 266 and raising free end 252 above rim 122 so that free end 252 can pivot about pivot 266 and away from lid 120.

Referring back to FIG. 14, a handle assembly 260 is pivotally connected to side wall 106. Handle assembly 260 includes a frame 262 that is connected directly to sidewall 106, such as by rivets, chemical bonding, or other suitable connection mechanism. A channel 264 is connected to frame 262. Channel 264 supports a pivoting end 266 of a handle 268. Pivoting end 266 of handle 268 is wider than lid lock 212 so that handle 268 can extend around an outer perimeter of lid lock 212, as shown in FIG. 4. Handle 268 is generally "U-shaped", with ends that extend loosely into channel 264 so that handle 268 can pivot about 180 degrees within channel 264 from the position shown in FIG. 4 to a position where handle 268 extends below lid lock 212.

Also provided are methods for assembling and using the sterilization systems and kits including the sterilization container, cases to be positioned within the sterilization container, and medical devices and instruments configured to be received within the graphic cases and sterilized, for example, using an autoclave process.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A locking mechanism comprising:
a shell;
a first clip slidingly inserted inside the shell, the first clip having a first locking member;
a second clip slidingly inserted inside the shell, the second clip having a second locking member; and
a first biasing member having a first end connected to the first clip and a second end connected to the second clip; and
a second biasing member connected between the first and second clips such that the first and second biasing members are laterally offset from each other from a longitudinal axis, and first and second biasing members bias the first clip and the second clip so that the first locking member is biased toward the second locking member.

2. The locking mechanism according to claim 1, wherein the first clip is identical to the second clip.

3. The locking mechanism according to claim 2, wherein the first locking member comprises a planar surface having a cavity formed at a proximal end thereof.

4. The locking mechanism according to claim 1, wherein the shell comprises a first activation opening and wherein the first clip comprises a first button slidably extending through the first activation opening.

5. The locking mechanism according to claim 4, wherein the first clip comprises a first body having a first proximal end connected to the button and a first distal end having a first biasing member support.

6. The locking mechanism according to claim 5, wherein the first proximal end comprises a first base and wherein the first distal end further comprises the first locking member.

7. The locking mechanism according to claim 6, wherein the first biasing member is disposed between the first base and the first locking member.

8. The locking mechanism according to claim 4, wherein the shell comprises an elongate cavity and wherein the first clip and the second clip are disposed inside the cavity.

9. A locking mechanism comprising:
a shell having a first opening, a second opening, and a cavity extending between the first opening and the second opening, the cavity having a longitudinal axis;
a first clip having:
a first button extending through the first opening;
a first elongate base extending distally from the first button;
a first spacer extending from the first elongate base;
a first surface extending upwardly from the first spacer, the first surface having a first cavity formed at a first proximal end thereof; and
a first biasing member support disposed between the first elongate base and the first surface;
a second clip having:
a second button extending through the second opening;
a second elongate base extending distally from the second button;
a second spacer extending from the second base;
a second surface extending upwardly from the second spacer, the second surface having a second cavity formed at a second proximal end thereof; and
a second biasing member support disposed between the second elongate base and the second surface; and
a biasing member laterally offset from the longitudinal axis, the biasing member having a first end connected to the first biasing member support and a second end connected to the second biasing member support.

10. The locking mechanism according to claim 9, wherein the biasing member biases the first surface toward the second surface.

11. The locking mechanism according to claim 10, wherein the first cavity and the second cavity form a locking surface.

12. The locking mechanism according to claim 9, wherein the first biasing member is disposed between the first elongate base and the first surface.

13. The locking mechanism according to claim 9, wherein the first surface is coplanar with the second surface.

14. The locking mechanism according to claim 9, wherein the first member is identical to the second member.

15. The locking mechanism according to claim 9, further comprising a mounting post disposed between the first cavity and the second cavity wherein, when the locking mechanism is in a locked position, the first surface and the second surface engage the mounting post.

16. A locking assembly comprising:
a mounting post; and
a locking mechanism comprising:
a shell;
a first clip having a longitudinal axis slidingly inserted inside the shell, the first clip having a first locking member disposed on a first side of the mounting post;
a second clip slidingly inserted inside the shell, the second clip being identical to the first clip and being disposed on an opposing side of the mounting post; and
a biasing member being laterally offset from the longitudinal axis, the biasing member having a first end connected to the first clip and a second end connected to the second clip such that the biasing member biases the first locking member and the second locking member into engagement with the mounting post.

17. The locking assembly according to claim 16 wherein the first clip comprises a first button extending outwardly from the shell wherein translation of the first button into the shell moves the first locking member away from the mounting post.

18. The locking assembly according to claim 17, wherein the first clip comprises an elongate body having a first end connected to the button and a second end connected to a biasing support member such that the first end of the biasing member is connected to the biasing support member.

19. The locking assembly according to claim 16, wherein the first locking member has a cavity such that the cavity extends partially around the mounting post when the biasing member biases the first locking member into engagement with the mounting post.

20. The locking assembly according to claim 16, wherein a first portion of the biasing member extends through the first latching member and wherein a remaining portion of the biasing member extends through the second latching member.

* * * * *